United States Patent
Fouque et al.

(10) Patent No.: US 10,457,749 B2
(45) Date of Patent: Oct. 29, 2019

(54) METHODS OF PURIFYING BISPECIFIC ANTIBODIES

(71) Applicant: NovImmune SA, Geneva (CH)

(72) Inventors: Nicolas Fouque, Cernex (FR); Jean François Depoisier, Mont Saxonnex (FR); Keith Wilson, Gwent (GB); Judith Vajda, Leonberg (DE); Egbert Müller, Darmstadt (DE); Romain Dabre, Darmstadt (DE)

(73) Assignee: NovImmune SA, Geneva (CH)

( * ) Notice: Subject to any disclaimer, the term of this patent is extended or adjusted under 35 U.S.C. 154(b) by 418 days.

(21) Appl. No.: 15/068,916

(22) Filed: Mar. 14, 2016

(65) Prior Publication Data
US 2016/0264685 A1    Sep. 15, 2016

Related U.S. Application Data

(60) Provisional application No. 62/132,782, filed on Mar. 13, 2015.

(51) Int. Cl.
| C07K 16/46 | (2006.01) |
| C07K 1/36 | (2006.01) |
| C07K 1/16 | (2006.01) |
| C07K 1/22 | (2006.01) |
| C07K 1/20 | (2006.01) |
| C07K 16/00 | (2006.01) |
| C07K 16/24 | (2006.01) |
| C07K 16/28 | (2006.01) |

(52) U.S. Cl.
CPC .............. *C07K 16/468* (2013.01); *C07K 1/16* (2013.01); *C07K 1/165* (2013.01); *C07K 1/20* (2013.01); *C07K 1/22* (2013.01); *C07K 1/36* (2013.01); *C07K 16/00* (2013.01); *C07K 16/248* (2013.01); *C07K 16/249* (2013.01); *C07K 16/2866* (2013.01); *C07K 2317/31* (2013.01); *C07K 2317/32* (2013.01); *C07K 2317/52* (2013.01)

(58) Field of Classification Search
None
See application file for complete search history.

(56) References Cited

U.S. PATENT DOCUMENTS

| 6,528,624 B1 | 3/2003 | Idusogie et al. |
| 2009/0191199 A1 | 7/2009 | Kanda et al. |
| 2013/0317200 A1* | 11/2013 | Elson ............... C07K 16/00 530/387.3 |
| 2014/0072585 A1* | 3/2014 | Herigstad ............ C07K 16/00 424/177.1 |
| 2016/0376304 A1* | 12/2016 | Bertl ............... C07K 16/00 530/387.3 |

FOREIGN PATENT DOCUMENTS

| WO | WO 2007/108955 A1 | 9/2007 |
| WO | WO 2010/135558 A1 | 11/2010 |
| WO | WO 2011/084255 A2 | 7/2011 |
| WO | WO 2012/023053 A2 | 2/2012 |
| WO | WO 2013/088259 A2 | 6/2013 |

OTHER PUBLICATIONS

"Chromatographic Process Media Catalog", 2012, pp. 1-78 http://citenpl.internal.epo.org/wf/web/citenpl/citenpl.html?url=http%3A//galachem.ru/uploads/2015/09/Tosoh-Chromatographic-process-media.pdf.
Cole et al, "The EBV-Hybridoma Technique and its Application to Human Lung Cancer", Monoclonal Antibodies and Cancer Therapy, p. 77-96 (1985).
Cote R. et al. "Generation of human monoclonal antibodies reactive with cellular antigens", Proc Natl Acad Sci USA, vol. 80, p. 2026-2030 (1983).
Gupta S. et al. "Affinity chromatography and co-chromatography of bispecific monoclonal antibody immunoconjugates", Journal of Biochemical and Biophysical Methods, vol. 51, p. 203-216 (2002).
Kozbor D. et al. "The production of monoclonal antibodies from human lymphocytes", Immunology Today, vol. 4, No. 3, p. 72-79 (1983).
Strohl, "Optimization of Fc-mediated effector functions of monoclonal Antibodies", Current Opinion in Biotechnology, vol. 20, p. 685-691 (2009).
Suresh et al. "Bispecific Monoclonal Antibodies from Hybrid Hybridomas", Methods in Enzymology, 121: 210 (1986).
Van der Neut Kolfschoten M. et al., "Anti-Inflammatory Activity of Human IgG4 Antibodies by Dynamic Fab Arm Exchange", Science 317:1554-1557 (2007).

* cited by examiner

*Primary Examiner* — Daniel E Kolker
*Assistant Examiner* — James L Rogers
(74) *Attorney, Agent, or Firm* — Cooley LLP; Ivor R. Elrifi; Cynthia A. Kozakiewicz

(57) ABSTRACT

The invention relates to the purification of bispecific antibodies carrying a different specificity for each binding site of the immunoglobulin molecule from a mixture of monospecific antibodies. The bispecific antibodies are composed of a single heavy chain and two different light chains, one containing a Kappa constant domain and the other a Lambda constant domain. This invention in particular relates to the isolation of these bispecific antibodies from mixtures that contain monospecific antibodies having two Kappa light chains or portions thereof and monospecific antibodies having two Lambda light chains or portions thereof. The invention also provides the methods of efficiently purifying these bispecific antibodies.

16 Claims, 8 Drawing Sheets

FIGURE 1A
FIGURE 1B
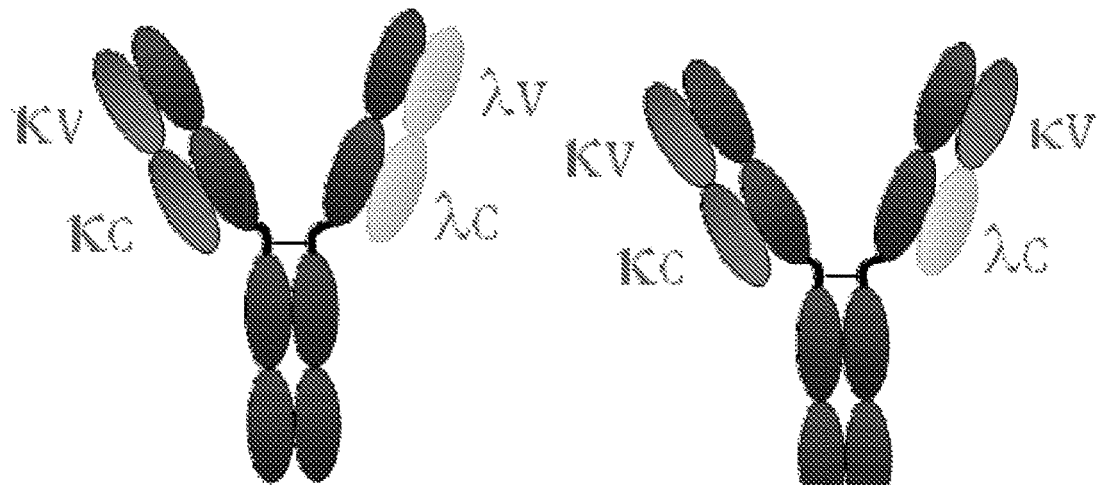
Common H
Common H
FIGURE 1C
Common H
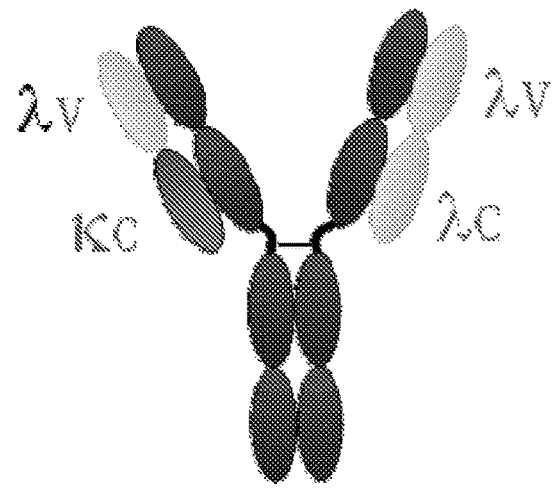
Common H

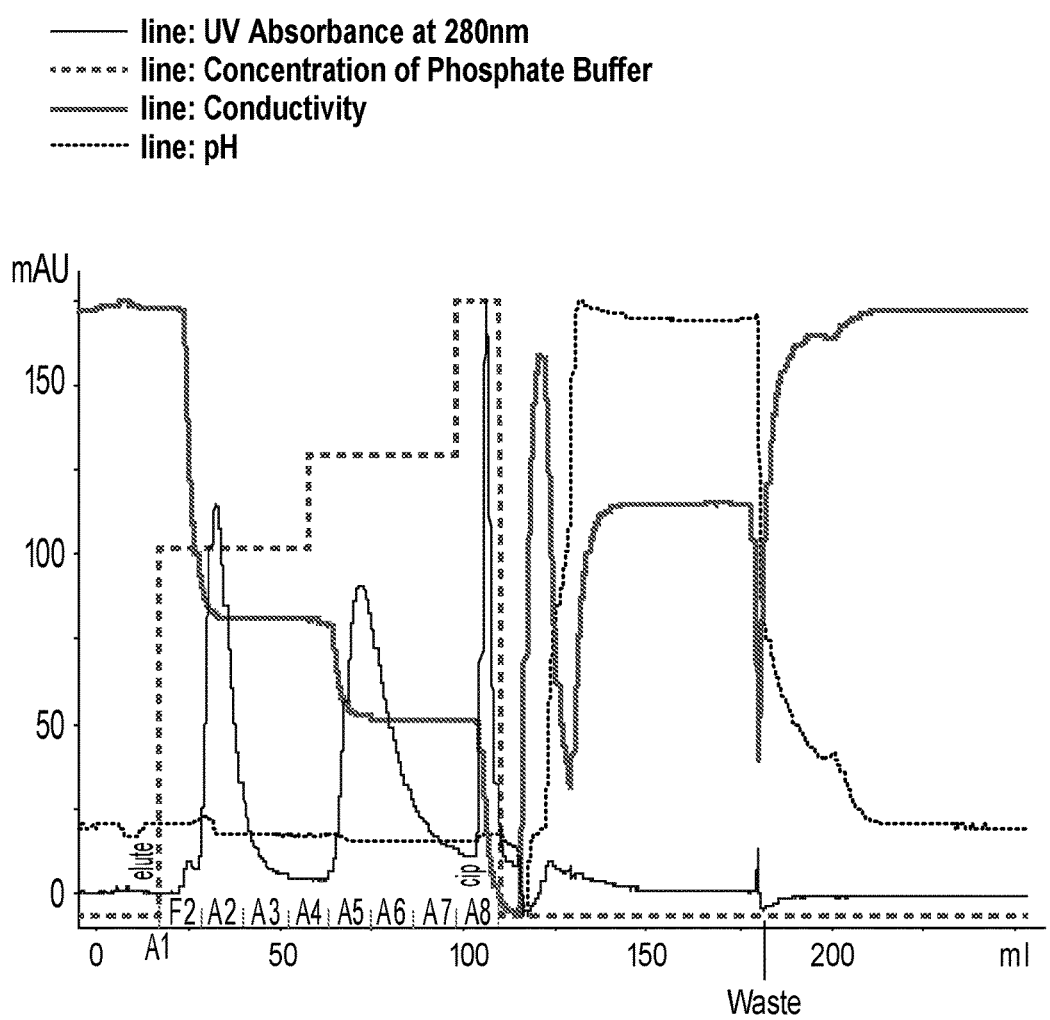

1: marker
2: starting material
3: first peak
4: second peak
5: third peak
6: internal reference 1: starting material
2: first peak
3: second peak
4: third peak
5: internal reference
6: marker

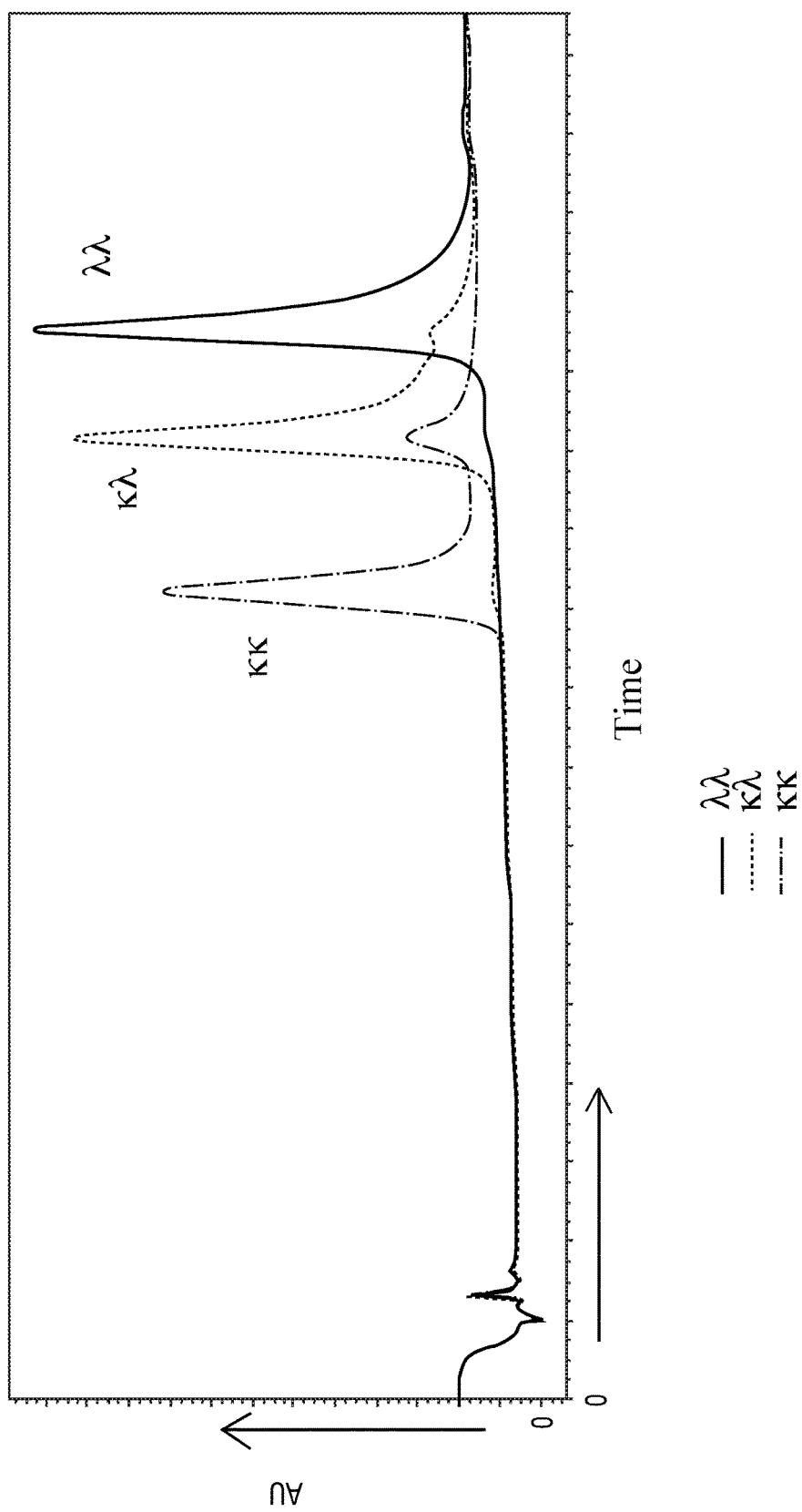

METHODS OF PURIFYING BISPECIFIC ANTIBODIES

RELATED APPLICATIONS

This application claims the benefit of U.S. Provisional Application No. 62/132,782, filed Mar. 13, 2015 the contents of which are incorporated herein by reference in their entirety.

FIELD OF THE INVENTION

The invention relates to the purification of bispecific antibodies carrying a different specificity for each binding site of the immunoglobulin molecule from a mixture of monospecific antibodies. The bispecific antibodies are composed of a single heavy chain and two different light chains, one containing a Kappa constant domain and the other a Lambda constant domain. This invention in particular relates to the isolation of these bispecific antibodies from mixtures that contain monospecific antibodies having two Kappa light chains or portions thereof and monospecific antibodies having two Lambda light chains or portions thereof. The invention also provides the methods of efficiently purifying these bispecific antibodies.

BACKGROUND OF THE INVENTION

An antibody is composed of four polypeptides: two heavy chains and two light chains. The antigen binding portion of an antibody is formed by the light chain variable domain (VL) and the heavy chain variable domain (VH). At one extremity of these domains six loops form the antigen binding site and also referred to as the complementarity determining regions (CDR). Three CDRs are located on the VH domain (H1, H2 and H3) and the three others are on the VL domain (L1, L2 and L3). During B cell development a unique immunoglobulin region is formed by somatic recombination known as V(D)J recombination. The variable region of the immunoglobulin heavy or light chain is encoded by different gene segments. The heavy chain is encoded by three segments called variable (V), diversity (D) and joining (J) segments whereas the light chain variable is formed by the recombination of only two segments V and J. A large number of antibody paratopes can be generated by recombination between one of the multiple copies of the V, D and J segments that are present in the genome. The V segment encodes the CDR1 and CDR2 whereas the CDR3 is generated by the recombination events. During the course of the immune response further diversity is introduced into the antigen binding site by a process called somatic hypermutation (SHM). During this process point mutations are introduced in the variable genes of the heavy and light chains and in particular into the regions encoding the CDRs. This additional variability allows for the selection and expansion of B cells expressing antibody variants with improved affinity for their cognate antigen.

The vast majority of immunoglobulins are bivalent and monospecific molecules carrying the same specificity on both arms as they are composed of two identical heavy chain polypeptides and two identical light chain polypeptides. However, it was recognized very early during the development of hybridoma technology that hybrid hybridomas can be created by a fusion event between two hybridomas (Suresh M R et al., Methods Enzymol 1986; 121: 210-228). These 'quadromas' express two different heavy and two different light chains and therefore produce a variety of different antibody species resulting from the random pairing of the heavy and light chains. Amongst these different species, bispecific antibodies (bsAbs) are generated, carrying a different specificity on each arm. Another naturally occurring exception is the immunoglobulin of the IgG4 isotype that is able to undergo heavy chain exchange due to a less stable dimerization mediated by the hinge region of that isotype (van der Neut Kolfschoten M et al., Science. 2007 317(5844):1554-7). Although this exchange seems to happen in vivo, its biological significance remains unclear.

Monospecific antibodies have emerged as a successful and attractive class of molecules for therapeutic intervention in several areas of human disease. However, targeting or neutralizing a single protein is not always sufficient to achieve efficacy in certain diseases which limits the therapeutic use of monospecific antibodies. It is increasingly clear that in a number of indications neutralizing one component of a biological system is not sufficient to achieve efficacy. One solution to this problem is the co-administration of several monospecific antibodies. This approach is however complicated by regulatory aspects if the antibodies to be combined have not been previously approved individually. Moreover, combination approaches are also costly from a manufacturing perspective. Accordingly, there exists a need for antibodies and therapeutics that enable targeting of multiple antigens with a single molecule.

SUMMARY OF THE INVENTION

The invention allows for the purification of bispecific antibodies that are undistinguishable in sequence from standard antibodies. The unmodified nature of the purified antibodies provides them with favorable manufacturing characteristics similar to standard monospecific antibodies.

The methods provided herein are useful for purifying a variety of bispecific antibodies particularly the bispecific antibodies referred to herein as "κλ-bodies" (kappa lambda-bodies), which have a common IgG heavy chain and two different light chains, one having a kappa (κ) constant region and the other having a lambda (λ) constant region, that drive specificity for two independent targets. The methods provided herein are useful from purifying these bispecific κλ-bodies from mixtures that contain monospecific antibodies having two Kappa light chains or portions thereof, also referred to herein as "κ monospecific antibodies" or "κ mono-Abs," and monospecific antibodies having two Lambda light chains or portions thereof, also referred to herein as "λ monospecific antibodies" or "λ mono-Abs."

The bispecific antibodies thereof to be purified can be generated using any of a variety of methods. For example, the bispecific antibodies and can be generated by (i) isolating two antibodies having different specificities and sharing the same variable heavy chain domain but different variable light chains, for example by using antibody libraries having a fixed heavy chain or transgenic animals containing a single VH gene; (ii) fusing the variable heavy chain domain to the constant region of a heavy chain, fusing one light chain variable domain to a Kappa constant domain, and fusing the other variable light chain domain to a Lambda constant domain; and (iii) co-expressing the three chains in a host cell or cell line, for example, mammalian cells and/or mammalian cell lines, leading to the assembly and secretion in the supernatant of a mixture of three antibodies: two monospecific antibodies and one bispecific antibody carrying two different light chains. In some antibodies produced using this method, at least a first portion of the first light chain is of the Kappa type and at least a portion of the second light chain is of the Lambda type. In some antibodies produced using this method, the first light chain includes at least a Kappa constant region. In some antibodies produced using this method, the first light chain further includes a Kappa variable region. In some antibodies produced using this method, the first light chain further includes a Lambda variable region. In some antibodies produced using this method, the second light chain includes at least a Lambda constant region. In some antibodies using this method, the second light chain further includes a Lambda variable region. In some antibodies using this method, the second light chain further includes a Kappa variable region. In some antibodies produced using this method, the first light chain includes a Kappa constant region and a Kappa variable region, and the second light chain includes a Lambda constant region and a Lambda variable region. In some antibodies produced using this method, the constant and variable framework region sequences are human.

The bispecific antibodies made using this method or any other suitable method known in the art are purified using standard chromatography techniques used for antibody purification. The bispecific antibodies generated using this method or any other suitable method known in the art can also be purified using other separation techniques, such as by way of non-limiting and non-exhaustive example, membrane filtration techniques and protein precipitation techniques. In a preferred embodiment, the bispecific antibody (or antibodies) is purified using multimodal chromatography, also known as mixed mode chromatography, or using hydrophobic interaction chromatography.

The invention provides methods of purifying a bispecific antibody from a mixture of antibodies by (a) providing a mixed antibody composition that comprises at least one bispecific antibody with a different specificity in each combining site and two copies of a single heavy chain polypeptide, a first light chain with a kappa constant region, and a second light chain with a lambda constant region (κλ-body); and one or more of the following: (i) at least one monospecific antibody having two lambda light chains or portions thereof (λ mono-Ab); and/or (ii) at least one monospecific antibody having two kappa light chains or portions thereof (κ mono-Ab); (b) providing a separation means; (c) contacting the separation means with the mixed antibody composition under conditions that allow for differential binding to the separation means by the κλ-body as compared to the binding to the separation means by the κ mono-Ab and/or the λ mono-Ab; and (d) eluting the κλ-body, κ mono-Ab, and/or the λ mono-Ab from the separation means under conditions that allow for preferential detachment of the κλ-body from the separation means as compared to detachment of κ mono-Ab and/or of the λ mono-Ab from the separation means.

In some embodiments, the mixed antibody composition includes at least one κλ-body and at least one λ mono-Ab. In some embodiments, the mixed antibody composition includes at least one κλ-body and κ mono-Ab. In some embodiments, the mixed antibody composition includes at least the following: (i) at least one κλ-body; (ii) at least one λ mono-Ab; and (iii) κ mono-Ab.

In some embodiments, the methods use a single separation means to separate bispecific κλ-bodies from κ mono-Abs and/or λ mono-Abs by differentially binding each of the three antibody species. In some embodiments, the methods use a single separation means to separate bispecific κλ-bodies from κ mono-Abs and/or λ mono-Abs through differential elution of each of the three antibody species from the separation means. In some embodiments, the methods use a single separation means to separate bispecific κλ-bodies from κ mono-Abs and/or λ mono-Abs by differentially binding each of the three antibody species followed by differential elution of each of the three antibody species from the separation means.

In some embodiments, purification of the κλ-body is performed by sequential binding to affinity chromatography followed by hydrophobic interaction chromatography. In some embodiments, purification of the κλ-body is performed by sequential binding to Protein A chromatography followed by hydrophobic interaction chromatography. In some embodiments, the affinity chromatography is Protein A chromatography. In some embodiments, the affinity chromatography is any art-recognized affinity chromatography technique other than Protein A chromatography, such as, by way of non-limiting example, chromatography techniques based on the use of Protein A mimetics or other affinity proteins. In some embodiments, the affinity chromatography, e.g., Protein A chromatography or any art-recognized affinity chromatography technique other than Protein A chromatography, is performed on a biological sample. In some embodiments, the biological sample is cell supernatant. In some embodiments, the cell is transfected with a κλ bispecific expression vector that includes at least one γ1 heavy chain cDNA sequence, one κ light chain cDNA sequence, and one λ cDNA sequence.

In some embodiments, purification of the κλ-body is performed by sequential binding to affinity chromatography followed by multimodal chromatography, also known as mixed mode chromatography. In some embodiments, purification of the κλ-body is performed by sequential binding to Protein A chromatography followed by multimodal chromatography. In some embodiments, the affinity chromatography is Protein A chromatography. In some embodiments, the affinity chromatography is any art-recognized affinity chromatography technique other than Protein A chromatography, such as, by way of non-limiting example, chromatography techniques based on the use of Protein A mimetics or other affinity proteins. In some embodiments, the affinity chromatography, e.g., Protein A chromatography or any art-recognized affinity chromatography technique other than Protein A chromatography, is performed on a biological sample. In some embodiments, the biological sample is cell supernatant. In some embodiments, the cell is transfected with a κλ bispecific expression vector that includes at least one γ1 heavy chain cDNA sequence, one κ light chain cDNA sequence, and one λ cDNA sequence.

In some embodiments, purification of the κλ-body is performed by sequential binding to affinity chromatography followed by hydrophobic interaction chromatography (HIC) followed by multi modal (mixed mode) chromatography. In some embodiments, the affinity chromatography is Protein A chromatography. In some embodiments, the affinity chromatography is any art-recognized affinity chromatography technique other than Protein A chromatography, such as, by way of non-limiting example, chromatography techniques based on the use of Protein A mimetics or other affinity proteins. In some embodiments, the affinity chromatography, e.g., Protein A chromatography or any art-recognized affinity chromatography technique other than Protein A chromatography, is performed on a biological sample. In some embodiments, the biological sample is cell supernatant. In some embodiments, the cell is transfected with a κλ bispecific expression vector that includes at least one γ1 heavy chain cDNA sequence, one κ light chain cDNA sequence, and one λ cDNA sequence.

In some embodiments, purification of the κλ-body is performed by sequential binding to Protein A chromatography followed by multi modal (mixed mode) chromatography followed by hydrophobic interaction chromatography (HIC). In some embodiments, the affinity chromatography, e.g., Protein A chromatography or any art-recognized affinity chromatography technique other than Protein A chromatography, is performed on a biological sample. In some embodiments, the biological sample is cell supernatant. In some embodiments, the cell is transfected with a κλ bispecific expression vector that includes at least one γ1 heavy chain cDNA sequence, one κ light chain cDNA sequence, and one λ cDNA sequence.

In some embodiments, the separation means is a resin, a membrane, a magnetic bead, a particle or a monolith.

In some embodiments, the separation means is multi-modal chromatography, also known as mixed mode chromatography. In some embodiments, the separation means is hydrophobic interaction chromatography.

In some embodiments, the separation means is a mixed mode chromatography resin. In some embodiments, the mixed mode chromatography resin is a TOYOPEARL® MX-Trp 650M resin (Tosoh Bioscience LLC). TOYOPEARL® MX-Trp-650M is based on the methacrylic polymer backbone of TOYOPEARL® media and uses tryptophan as the active ligand.

In some embodiments, the separation means is a hydrophobic interaction chromatography resin. In some embodiments, the hydrophobic interaction chromatography resin is a TOYOPEARL® Butyl 600M resin (Tosoh Bioscience LLC). TOYOPEARL® Butyl 600M resin is based on the methacrylic polymer backbone of TOYOPEARL® media and includes a butyl ligand.

In some embodiments, the separation means is a combination of at least two resins. In some embodiments, the separation means is a combination of at least two mixed mode chromatography resins. In some embodiments, the separation means is a combination of more than two mixed mode chromatography resins, e.g., three or more, four or more, and/or five or more mixed mode chromatography resins. In some embodiments, the separation means is a combination of at least two hydrophobic interaction chromatography resins. In some embodiments, the separation means is a combination of more than two hydrophobic interaction chromatography resins, e.g., three or more, four or more, and/or five or more hydrophobic interaction chromatography resins. In some embodiments, the separation means is a combination of at least one mixed mode chromatography resin and at least one hydrophobic interaction chromatography resin.

In some embodiments, the separation means includes the use of a mixed mode chromatography resin followed by the use of a hydrophobic interaction chromatography resin. In some embodiments, the separation means includes the use of a TOYOPEARL® MX-Trp 650M resin (Tosoh Bioscience LLC) followed by the use of a TOYOPEARL® Butyl 600M resin (Tosoh Bioscience LLC).

In some embodiments, the separation means includes the use of a hydrophobic interaction chromatography resin followed by the use of a mixed mode chromatography resin. In some embodiments, the separation mean includes the use of a TOYOPEARL® Butyl 600M resin (Tosoh Bioscience LLC) followed by the use of a TOYOPEARL® MX-Trp 650M resin (Tosoh Bioscience LLC).

In some embodiments, the binding and/or elution conditions include a step variation in the pH level and/or a step variation in conductivity corresponding to salt concentration variation. In some embodiments, the binding and/or elution conditions include a step variation in the inorganic salt concentration such as sodium chloride (NaCl) concentration or the concentration of other inorganic salts such as by way of non-limiting and non-exhaustive example, inorganic salt combinations from the Hofmeister series of ions, for example, a sulfate. In some embodiments, the methods include the step of varying the concentration of ammonium sulfate for binding and/or elution. In some embodiments, the methods include the further step of determining the purity and proportions of bispecific antibody, κ mono-Ab and/or λ mono-Ab in the eluted fraction. This step can be accomplished using any of a variety of art-recognized techniques, such as by way of non-limiting and non-exhaustive example, hydrophobic interaction-high performance liquid chromatography (HIC-HPLC), ion exchange-high performance liquid chromatography (IEX-HPLC), cation exchange-high performance liquid chromatography (CEX-HPLC) or reverse phase-high performance liquid chromatography (RP-HPLC).

The Examples provided herein demonstrates the feasibility of using a higher salt or a lower salt step elution to preferentially elute bispecific antibody from the TOYOPEARL® MX-Trp-650M mixed mode chromatography or the hydrophobic interaction resin TOYOPEARL® Butyl 600M resin over κ mono-Ab and/or λ mono-Ab, and additionally, the feasibility of using a combination of mixed mode chromatography and hydrophobic interaction chromatography. For example, a lower salt step elution, e.g., lowering the concentration of ammonium sulfate, is used to preferentially elute bispecific antibody from the hydrophobic interaction resin TOYOPEARL® Butyl 600M resin over κ mono-Ab and/or λ mono-Ab.

BRIEF DESCRIPTION OF THE DRAWINGS

FIGS. 1A, 1B, and 1C are a series of schematic representations of the structure of different κλ-body bispecific antibodies composed of two copies of a unique heavy chain polypeptide and two different light chain polypeptides. FIG. 1A depicts a Kappa variable domain fused to a Kappa constant domain and a Lambda variable domain fused to Lambda constant domain. FIG. 1B depicts Kappa variable domains fused to a Kappa constant domain and a Lambda constant domain. FIG. 1C depicts Lambda variable domains fused to a Kappa constant domain and a Lambda constant domain.

FIG. 3A is a graph depicting a representative UV absorbance trace profile of TOYOPEARL® Butyl 600M using buffer step gradient elution.

FIG. 3E is a graph depicting HIC-HPLC analysis of TOYOPEARL® MX-Trp 650M fractions.

DETAILED DESCRIPTION

Figure 2:
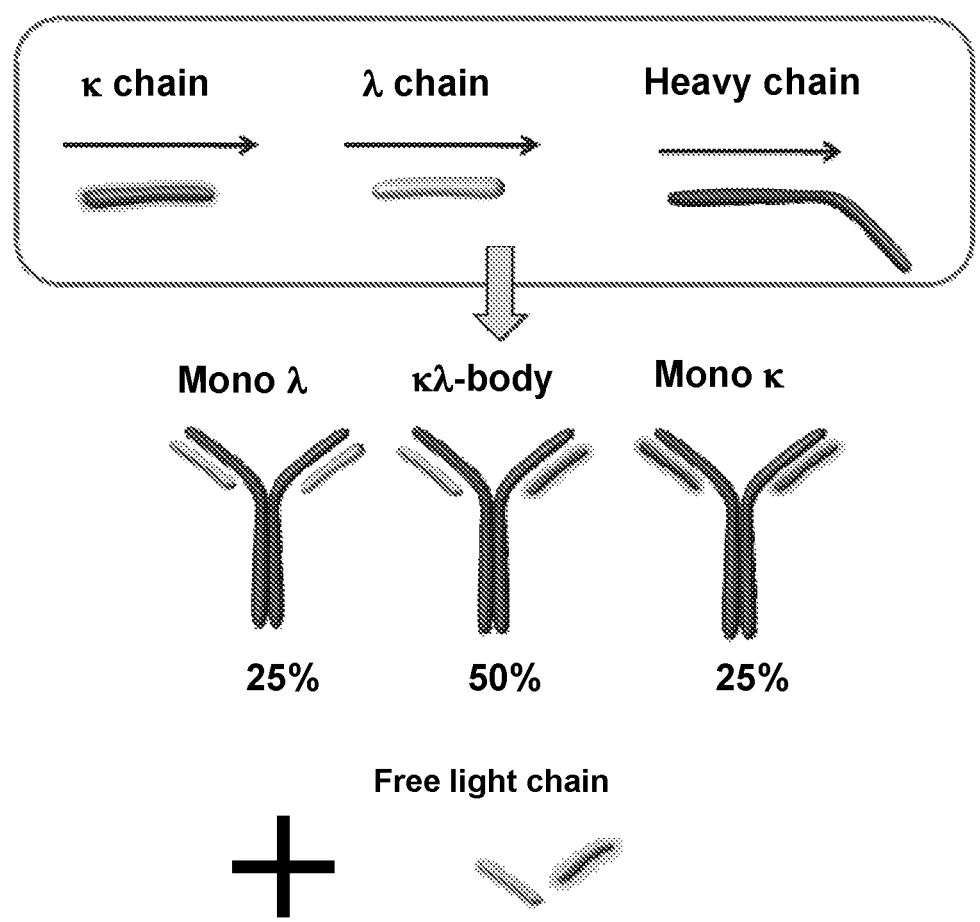
FIG. 2 is an illustration depicting that the expression of tri-cistronic expression vector in CHO cells gives rise to three antibody products with a theoretical 25:50:25 ratio.

The present invention provides methods of purifying bispecific antibodies that are identical in structure to a human immunoglobulin. This type of molecule is composed of two copies of a unique heavy chain polypeptide, a first light chain variable region fused to a constant Kappa domain and second light chain variable region fused to a constant Lambda domain. Each combining site displays a different antigen specificity to which both the heavy and light chain contribute. The light chain variable regions can be of the Lambda or Kappa family and are preferably fused to a Lambda and Kappa constant domain, respectively. This is preferred in order to avoid the generation of non-natural polypeptide junctions. However it is also possible to obtain bispecific antibodies of the invention by fusing a Kappa light chain variable domain to a constant Lambda domain for a first specificity and fusing a Lambda light chain variable domain to a constant Kappa domain for the second specificity (FIGS. 1A-1C). The bispecific antibodies described herein are also referred to as IgG κλ antibodies or "κλ bodies," a fully human bispecific IgG format. This κλ-body format allows the affinity purification of a bispecific antibody that is indistinguishable from a standard monospecific antibody, e.g., a standard IgG molecule, therefore, favorable as compared to previous formats.

The locations and/or arrangements of the Kappa light chain and the Lambda light chain (or portions thereof) shown in these figures are not intended to be limiting. Those of ordinary skill in the art will appreciate that the Kappa light chain and the Lambda light chain (or portions thereof) can also be arranged so as to produce the mirror-image of the bispecific antibodies shown in FIGS. 1A-1C. Those of ordinary skill in the art will also appreciate that the bispecific antibodies that are represented in a full IgG format in FIGS. 1A-1C can also be generated using other immunoglobulin isotypes or in other immunoglobulin formats such as F(ab')$_2$.

The κλ-bodies are generated by identifying two antibody Fv regions (each composed by a variable light chain and variable heavy chain domain) having different antigen specificities that share the same heavy chain variable domain.

The κλ-bodies to be purified using the methods of the invention are generated using any of a variety of methods for generating antibodies. Numerous methods have been described for the generation of antibodies and fragments thereof. (See, e.g., Antibodies: A Laboratory Manual, Harlow E, and Lane D, 1988, Cold Spring Harbor Laboratory Press, Cold Spring Harbor, N.Y., incorporated herein by reference). Fully human antibodies are antibody molecules in which the sequence of both the light chain and the heavy chain, including the CDRs 1 and 2, arise from human genes. The CDR3 region can be of human origin or designed by synthetic means. Such antibodies are termed "human antibodies" or "fully human antibodies" herein. Human monospecific antibodies can be prepared by using the trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In some embodiments, the κλ-bodies to be purified are generated, for example, using antibody libraries in which the heavy chain variable domain is the same for all the library members and thus the diversity is confined to the light chain variable domain. Such libraries are described, for example, in PCT Publication No. WO 2010/135558 and PCT Publication No. WO 2011/084255, each of which is hereby incorporated by reference in its entirety. However, as the light chain variable domain is expressed in conjunction with the heavy variable domain, both domains can contribute to antigen binding. To further facilitate the process, antibody libraries containing the same heavy chain variable domain and either a diversity of Lambda variable light chains or Kappa variable light chains can be used in parallel for in vitro selection of antibodies against different antigens. This approach enables the identification of two antibodies having a common heavy chain but one carrying a Lambda light chain variable domain and the other a Kappa light chain variable domain that can be used as building blocks for the generation of a bispecific antibody in the full immunoglobulin format of the invention. The bispecific antibodies to be purified using the methods of the invention can be of different isotypes and their Fc portion can be modified in order to alter the bind properties to different Fc receptors and in this way modify the effectors functions of the antibody as well as it pharmacokinetic properties. Numerous methods for the modification of the Fc portion have been described and are applicable to antibodies of the invention. (See for example Strohl, W R, "Optimization of Fc-mediated Effector Functions of Monoclonal Antibodies," Curr. Opin. Biotechnol., 2009 (6):685-91; U.S. Pat. No. 6,528,624; U.S. Patent Application Publication No. 2009/0191199). The methods of the invention can also be used to purify bispecific antibodies and antibody mixtures in a F(ab')$_2$ format that lacks the Fc portion.

Preferably, the κλ-bodies to be purified have been optimized for the co-expression of the common heavy chain and two different light chains into a single cell to allow for the assembly of a bispecific antibody of the invention. If all the polypeptides get expressed at the same level and get assembled equally well to form an immunoglobulin molecule then the ratio of monospecific (same light chains) and bispecific (two different light chains) should be 50%. However, it is likely that different light chains are expressed at different levels and/or do not assemble with the same efficiency. Furthermore, light chains that escape assembly into an intact IgG molecule may be secreted into the cell culture supernatant as "free-light chains". Means to modulate the relative expression of the different polypeptides to compensate for their intrinsic expression characteristics or different propensities to assemble with the common heavy chain include, by way of non-limiting examples, the use of promoter(s) with variable strength(s), the use of internal ribosome entry sites (IRES) featuring different efficiencies or other types of regulatory elements that can act at transcriptional or translational levels as well as acting on mRNA stability. The modulation of the expression can also be achieved by multiple sequential transfections of cells to increase the copy number of individual genes expressing one or the other light chain and thus modify their relative expressions.

The co-expression of the heavy chain and two light chains generates a mixture of three different antibodies secreted into the cell culture supernatant: two monospecific bivalent antibodies and one bispecific bivalent antibody. The latter has to be purified from the mixture to obtain the κλ-body of interest. Multi modal chromatography or mixed mode chromatography facilitates the purification of the κλ-body due to various mechanisms of interactions such as, by way of non-limiting example, ion exchange characteristics and hydrophobic characteristics, which confer high binding capacities and allow efficient purification of bispecific antibodies, including purification of κλ-bodies. The multi modal or mixed mode chromatography methods are efficient because multiple modes of chromatography are utilized simultaneously. Hydrophobic chromatography facilitates the purification of the κλ-body due to the hydrophobic characteristics which allow the efficient purification of specific antibodies. The combination of multi modal or mixed mode chromatography followed by hydrophobic chromatography facilitates the purification of the κλ-body due to multiple mechanisms of interactions applied sequentially, thus allowing even more efficient purification of bispecific antibodies than either mechanism alone.

The co-expression of the three chains led to the assembly of three different antibodies: two monospecific and one bispecific antibodies. Their theoretical relative ratios should be 1:1:2 provided the expression levels and assembly rates are similar for both light chains. The bispecific antibodies were purified using Protein A affinity chromatography procedure followed by either multi modal chromatography or hydrophobic chromatography or Protein A affinity chromatography followed by multi modal chromatography and hydrophobic chromatography.

Previous approaches to produce and purify bispecific antibody formats aimed at forcing the production of a homogenous bispecific molecule using different antibody engineering approaches were done at the expense of productivity, scalability and stability of the product. The methods described herein provide efficient means to purify bispecific antibodies.

In contrast to previous approaches to produce and purify bispecific antibody formats, the methods provided herein use a single separation means to separate bispecific κλ-bodies from κ mono-Abs and/or λ mono-Abs, by either differentially binding each of the three antibody species or through differential elution of each of the three antibody species from the separation means.

The methods provided herein are the first to use processes such as mixed mode chromatography and/or hydrophobic interaction chromatography and/or a combination of both these chromatography methods to separate bispecific antibodies having two different light chains, one containing a Kappa constant domain and the other a Lambda constant domain from monospecific antibodies having two Kappa light chains or portions thereof and monospecific antibodies having two Lambda light chains or portions thereof. In contrast, previous approaches such as, e.g., those in PCT Publication No. WO 2013/088259, were designed to remove intact, full length bispecific antibodies from non-intact antibodies such as the free light chains shown in FIG. 2. Thus, the methods provided herein are advantageous over previous approaches.

EXAMPLES

Example 1: Purification of Bispecific Antibodies Utilizing Hydrophobic Interaction Chromatography The κλ-body is a novel bispecific IgG format that includes a common IgG1 heavy chain and two different light chains that drive specificity for two independent targets. In order to allow for an efficient purification protocol applicable to large scale industrial processes, the format requires that one light chain contains a κ constant region whilst the other contains a λ constant region. (See FIGS. 1A-1C).

In order to produce κλ-body, the common heavy chain and two light chains are expressed in CHO cells using a triple gene expression vector. This vector format allows for the construction of three products: monospecific κ antibody (κ mono-Ab), bispecific κλ-body and monospecific λ antibody (λ mono-Ab). The theoretical product ratio is 25:50:25. (See FIG. 2).

In these studies, purification of this κλ-body format is performed by sequential binding to Protein A affinity chromatography followed by the hydrophobic interaction resin TOYOPEARL® Butyl 600M.

The studies provided herein demonstrate the successful separation of κλ-body from monospecific lambda and monospecific kappa antibodies (mono-Abs) using buffer step elution chromatography.

Start Material:

The clarified 25 L wave bag fermentation supernatant of a CHO cell transfected with a κλ bispecific expression vector (containing one γ1 heavy chain cDNA, one κ light chain cDNA and one λ light chain cDNA) was used as the starting material for Protein A chromatography followed by hydrophobic interaction chromatography.

Figure 3B:
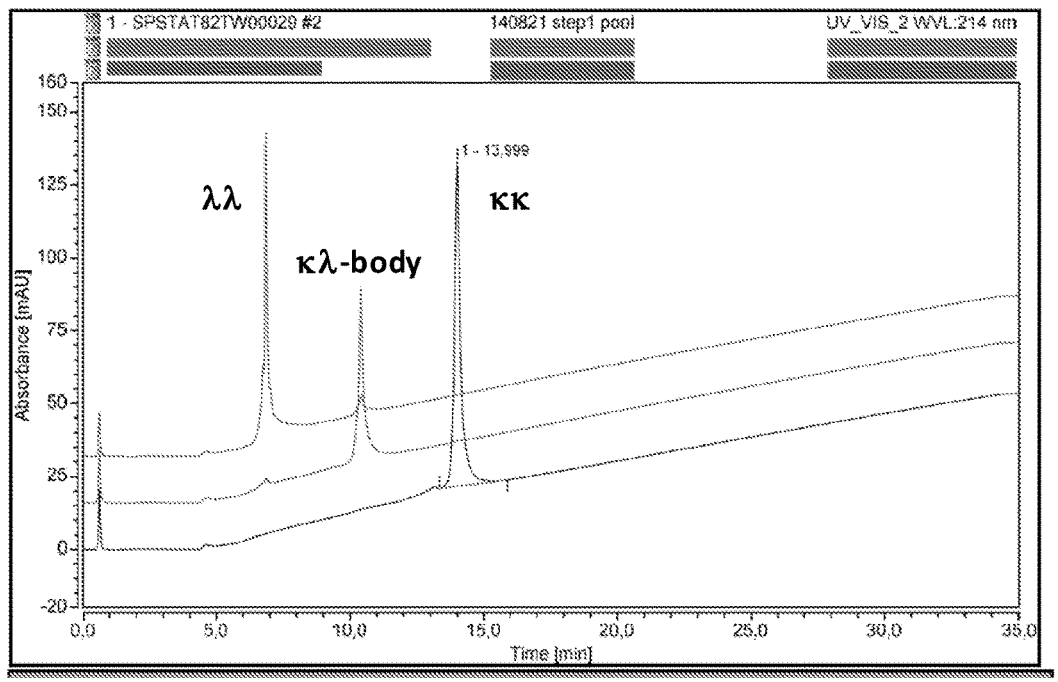
FIG. 3B is graph depicting an illustration of TOYOPEARL® Butyl 600M elution fractions analysis using CEX-HPLC.

Step:

κλ-body bispecific IgG antibody was purified using hydrophobic interaction chromatography (HIC) media (Tosoh Bioscience). After dilution 1:1 of the sample in 100 mM sodium phosphate 1M ammonium sulfate pH 7.0 buffer (equilibration buffer), the column was loaded at 10 mg/mL. After a wash step with equilibration buffer (5 column volumes), a step-elution was performed using a 10 mM Sodium Phosphate pH 7.0 buffer (60% and 75% in two sequential steps) (FIG. 3A). The eluted fractions were collected and analyzed by UV absorbance measurement at 280 nm (using a NanoDrop UV-Vis spectrophotometer, Thermo Scientific) in order to determine product recovery. Cation exchange performance liquid chromatography (CEX-HPLC) was performed in order to determine the ability of the purification process to separate the κλ-body bispecific IgG from the two monospecific antibody by-products (FIG. 3B).

Example 2: Purification of Bispecific Antibodies Utilizing Multimodal Mixed Mode Chromatography As described in Example 1, the κλ-body is a novel bispecific IgG format that includes a common IgG1 heavy chain and two different light chains that drive specificity for two independent targets. In order to allow for an efficient purification protocol applicable to large scale industrial processes, the format requires that one light chain contains a κ constant region whilst the other contains a λ constant region. (See FIGS. 1A-1C).

In order to produce κλ-body, the common heavy chain and two light chains are expressed in CHO cells using a triple gene expression vector. This vector format allows for the construction of three products: monospecific κ antibody (κ mono-Ab), bispecific κλ-body and monospecific λ antibody (λ mono-Ab). The theoretical product ratio is 25:50:25. (See FIG. 2).

In these studies, purification of this κλ-body format is performed by sequential binding to Protein A affinity chromatography followed by the mixed mode chromatography resin TOYOPEARL® MX-Trp 650 M.

The studies provided herein demonstrate the successful separation of κλ-body from monospecific lambda and monospecific kappa antibodies (mono-Abs) using NaCl step elution chromatography.

Start Material:

The clarified 25 L wave bag fermentation supernatant of a CHO cell transfected with a κλ bispecific expression vector (containing one γ1 heavy chain cDNA, one κ light chain cDNA and one λ light chain cDNA) was used as the starting material for Protein A chromatography followed by multi modal (mixed mode) interaction chromatography.

Figure 3C:
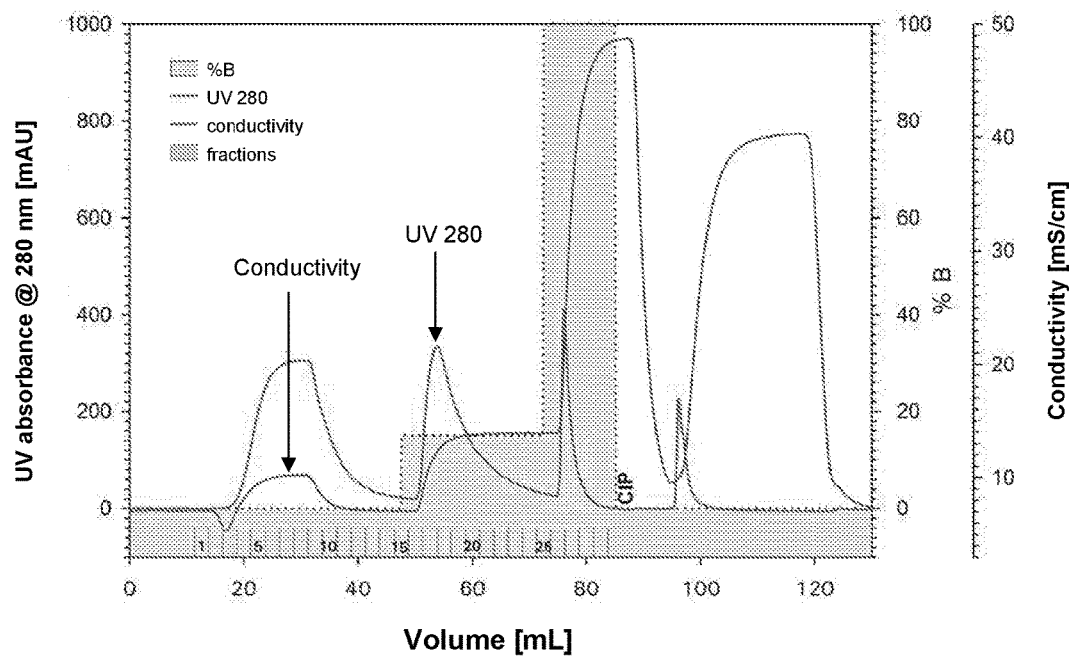
FIG. 3C is a graph depicting a representative UV absorbance trace profile of TOYOPEARL® MX-Trp 650 M using NaCl step gradient elution.
Figure 3D:
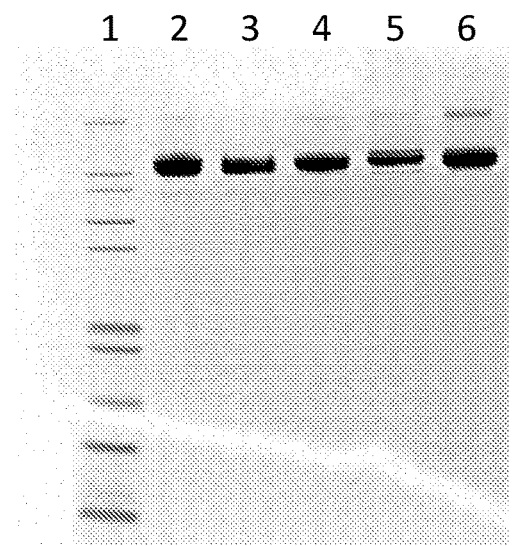
FIG. 3D is an illustration depicting non-reduced and reduced SDS-PAGE analysis of TOYOPEARL® MX-Trp 650M fractions.
Figure 3D:
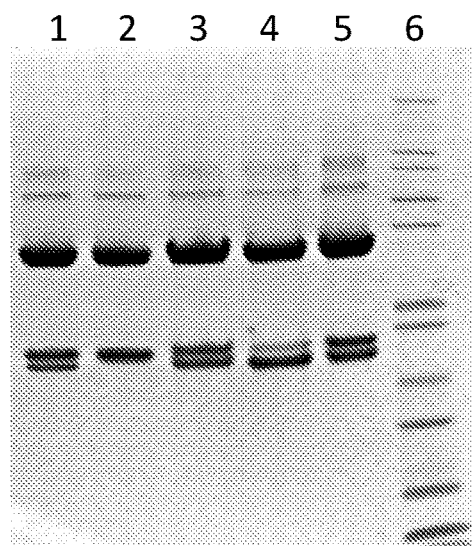

Step:

κλ-body bispecific IgG antibody was purified using multi modal (mixed mode) chromatography media (Tosoh Bioscience). After column loading at 25 mg/mL and a wash step with 100 mM Sodium Phosphate, pH 6.0. (5 column volumes), a NaCl step-elution was performed using a 100 mM Sodium Phosphate pH 6.0 buffer (15% and 100% of 500 mM NaCl buffer in two sequential steps (FIG. 3C). The flow through and eluted fractions were collected and analyzed by absorbance measurement at 280 nm (using a NanoDrop UV-Vis spectrophotometer, Thermo Scientific) in order to determine product recovery, reduced and non-reduced SDS-PAGE (using Invitrogen Novex NuPAGE 12-well 4-20% gradient gels following manufacturer's guidelines) in order to determine the purity and composition of the samples (FIG. 3D) and hydrophobic interaction-high performance liquid chromatography (HIC-HPLC) (FIG. 3E); in order to determine the ability of the purification process to separate the κλ-body bispecific IgG from the two monospecific antibody by-products.

As shown by the UV absorbance trace (red) in FIG. 3C, the step elutions applied to the TOYOPEARL® MX-Trp 650M chromatography mixed mode resin allowed for the sequential separation of three fractions. Reduced and non-reduced SDS-PAGE analysis of fractions collected during the mixed mode purification, shown in FIG. 3D revealed the high purity of the eluted fraction ($2^{nd}$ peak) at 15% of NaCl containing the κλ-body whereas the monospecific λ mono-Ab and κ mono-Ab IgGs were separated and collected in the non-retained fraction ($1^{st}$ peak) for the λλ and the 100% NaCl step fraction ($3^{rd}$ peak) for the κκ respectively. The three fractions were further characterized by HIC-HPLC analysis and subsequent integration of the peak areas of the HIC-HPLC chromatograms (FIG. 3E). The results summarized in Table 1 were in accordance with the SDS-PAGE analysis, demonstrating the high purity of the κλ-body (96%) in the $2^{nd}$ eluted fraction at 15% NaCl.

TABLE 1

UV peak integration of HIC-HPLC analysis of TOYOPEARL ® MX Trp-650M collected bound fractions

| Fractions | κ mono-Ab % | λ mono-Ab % | κλ-body % |
|---|---|---|---|
| Flow through | 0 | 99.5 | 0.5 |
| Step 15% | 2 | 2 | 96 |
| Step 100% | 85 | 15 | 0 |

Example 3: Purification of Bispecific Antibodies Utilizing Multi Modal Mixed Mode Chromatography Followed by Hydrophobic Chromatography As described in Example 1, the κλ-body is a novel bispecific IgG format that includes a common IgG1 heavy chain and two different light chains that drive specificity for two independent targets. In order to allow for an efficient purification protocol applicable to large scale industrial processes, the format requires that one light chain contains a κ constant region whilst the other contains a λ constant region. (See FIGS. 1A-1C).

In order to produce κλ-body, the common heavy chain and two light chains are expressed in CHO cells using a triple gene expression vector. This vector format allows for the construction of three products: monospecific κ antibody (κ mono-Ab), bispecific κλ-body and monospecific λ antibody (λ mono-Ab). The theoretical product ratio is 25:50:25. (See FIG. 2).

In this example, purification of this κλ-body format is performed by sequential binding to Protein A affinity chromatography followed multi modal (mixed mode) chromatography by the TOYOPEARL® MX-Trp 650M mixed mode resin followed by hydrophobic interaction chromatography using the TOYOPEARL® Butyl 600M resin.

Step:

Protein A affinity eluate containing κλ-body bispecific IgG antibody was purified using mixed mode chromatography media (Tosoh Bioscience) followed by hydrophobic interaction chromatography (HIC) media (Tosoh Bioscience). The TOYOPEARL® Butyl 600M column was loaded with the eluted sample purified with the mixed mode column (corresponding to fraction 2 in FIG. 4A) and diluted 1:1 in 100 mM sodium phosphate 1M ammonium sulfate pH 7.0 buffer) and after a wash step, a buffer step elution was performed to reduce the level of ammonium sulfate (FIG. 5A). The eluted fractions were collected and analyzed by UV absorbance measurement at 280 nm (using a NanoDrop UV-Vis spectrophotometer, Thermo Scientific) in order to determine product recovery, cation exchange-high performance liquid chromatography (CEX-HPLC) was performed in order to determine the ability of the purification process to separate the κλ-body bispecific IgG from the two monospecific antibody by-products (FIG. 5B).

Figure 4A:
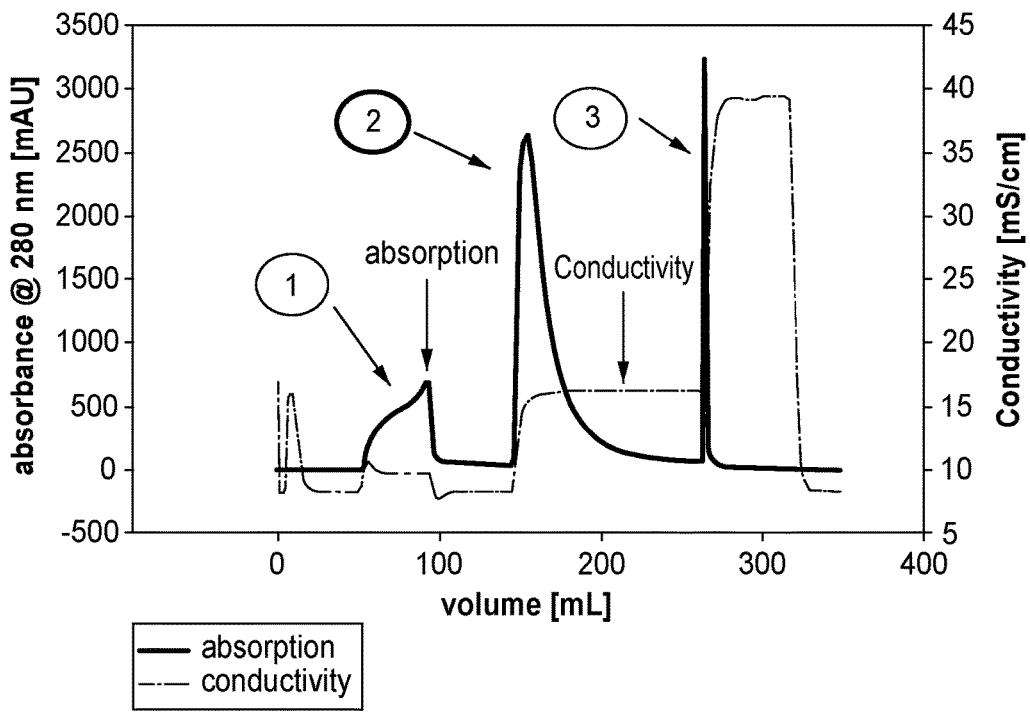
FIG. 4A is a graph depicting a representative UV absorbance trace profile of TOYOPEARL® MX-Trp 650M using NaCl step gradient elution obtained at larger column scale.
Figure 4B:
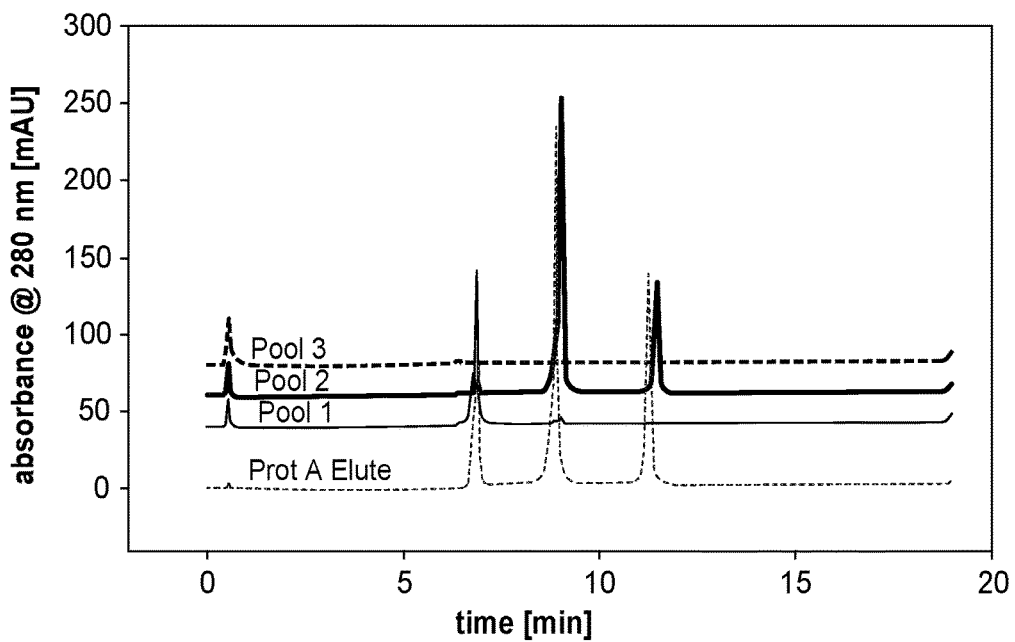
FIG. 4B is a graph depicting an illustration of TOYOPEARL® MX-Trp 650M elution fractions analysis using CEX-HPLC.
Figure 5A:
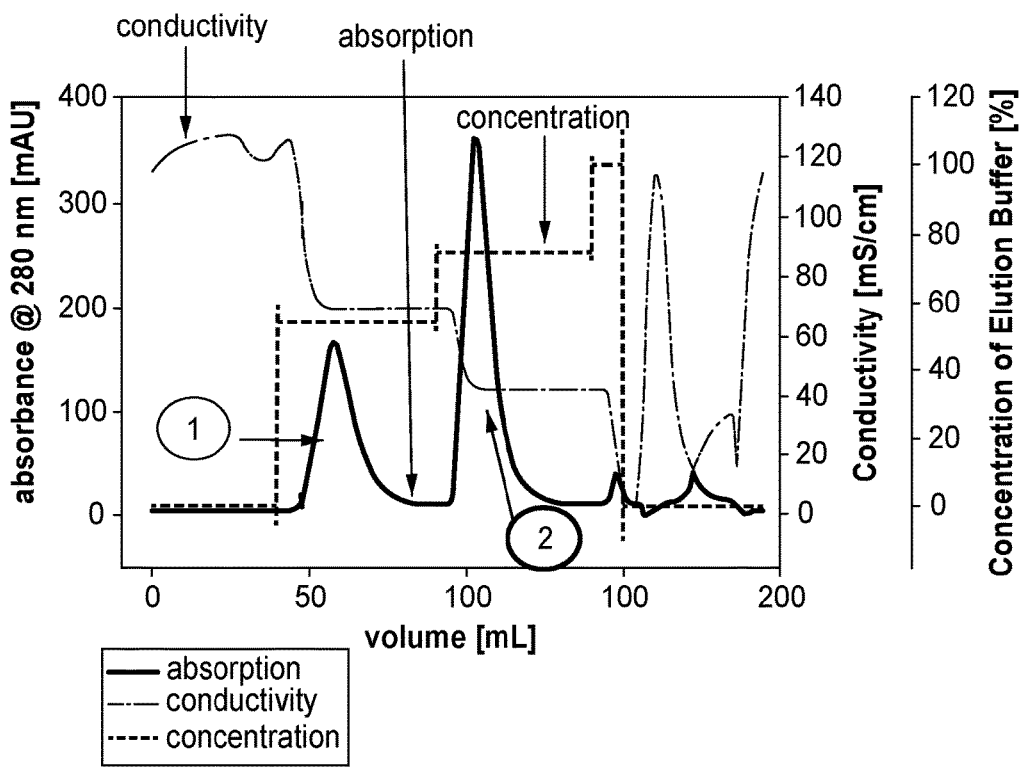
FIG. 5A is a graph depicting a representative UV absorbance trace profile of TOYOPEARL® Butyl 600M using NaCl step gradient elution at larger column scale.
Figure 5B:
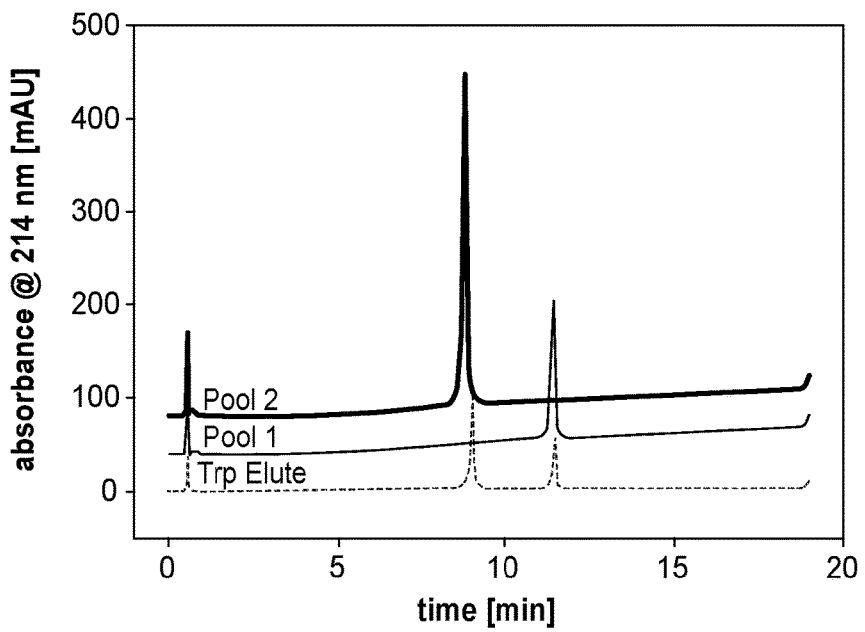
FIG. 5B is a graph depicting an illustration of TOYOPEARL® Butyl 600M elution fractions analysis using CEX-HPLC.

As shown by the UV absorbance trace (red) in FIG. 4A, the step elutions applied to the TOYOPEARL® MX-Trp 650M mixed mode chromatography resin allowed for the sequential separation of three fractions. CEX-HPLC analysis of fractions collected during the mixed mode purification confirmed the high purity of the eluted—κλ-body (FIG. 4B). The main fraction (pool 2) eluted at 20% NaCl in acetate pH 6.0 buffer was further loaded onto the TOYOPEARL® butyl 600M hydrophobic interaction chromatography resin. The results are depicted in FIG. 5A.

As shown by the UV absorbance trace (red) in FIG. 5A, the step elutions applied to the TOYOPEARL® Butyl 600M hydrophobic interaction chromatography resin allowed for the sequential separation of two fractions. CEX-HPLC (FIG. 5B) analysis of fractions confirmed the separation and purity of the κλ-body eluted in the $2^{nd}$ fraction in a step-elution performed using a 10 mM Sodium Phosphate pH 7.0 buffer (75%) and the remaining κκ-monospecific eluted in the first fraction in a step-elution performed using a 10 mM Sodium Phosphate pH 7.0 buffer (54%). The high purity of the main fraction (pool 2) corresponding to the κλ-body was measured to be >95%.

The data presented in these working examples demonstrates the feasibility of using a multimodal (mixed mode) chromatography or hydrophobic interaction chromatography or combination of multimodal (mixed mode) chromatography and hydrophobic interaction chromatography to purify bispecific antibodies from an IgG mixture, including κλ-bodies.

HIC-HPLC Method:

In order to determine the relative proportions of the λ mono-Ab, κ mono-Ab and the κλ-body in a sample mixture, a HIC-HPLC (hydrophobic interaction chromatography-high performance liquid chromatography) assay using a Dionex ProPac HIC-10 column was used. A descending gradient between 85 to 25% of ammonium sulfate was applied onto the column after the loading of the sample in order to elute the 3 species with high resolution, the κ mono-Ab eluting first, followed by the κλ-body and finally the λ mono-Ab. Peak area integration of the UV trace monitored at 280 nm was performed in order to determine the amount of each species.

CEX-HPLC Method:

This cation exchange-high performance liquid chromatography (CEX-HPLC) method was used to determine the proportions of monospecific and bispecific antibody in purified samples. The CEX-HPLC method allows for the separation of protein variants according to their charge distribution. Samples were prepared to load 50 μg onto A BioMab NP5-SS column (Agilent) and a linear gradient of 10 mM sodium phosphate, 500 mM NaCl, pH 6.5 (from 0% to 100% NaCl concentration) at a flow rate of 0.8 mL/min was applied in order to separate the different antibody products. UV detection at 214 nm was employed to monitor sample elution. The three populations were identified (according to reference standards) and analyzed according to their percentage relative area. The percentage of each isoform was determined by calculating the peak area of each component relative to the total peak area.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of purifying a bispecific antibody from a mixture of antibodies, the method comprising the steps of:
   (a) performing protein A chromatography on a biological sample to produce a mixed antibody composition comprising of (i) at least one bispecific antibody with a different specificity in each combining site and two copies of a single heavy chain polypeptide, a first light chain with a kappa constant region, and a second light chain with a lambda constant region (κλ-body); (ii) at least one monospecific antibody having two lambda light chains or portions thereof (λ mono-Ab); and (iii) at least one monospecific antibody having two kappa light chains or portions thereof (κ mono-Ab);
   (b) contacting the mixed antibody composition with a separation means under conditions that allow for differential binding to the separation means by the κλ-body as compared to the binding to the separation means by the κ mono-Ab and the λ mono-Ab, wherein the separation means comprises a combination of a hydrophobic interaction chromatography resin and a mix mode chromatography resin; and
   (c) eluting the κλ-body, the κ mono-Ab, and the λ mono-Ab from the separation means under conditions that allow for preferential detachment of the κλ-body from the separation means as compared to detachment of κ mono-Ab and of the λ mono-Ab from the separation means.

2. The method of claim 1, wherein the separation means is a resin, a membrane, a magnetic bead, a particle or a monolith.

3. The method of claim 1, wherein the binding conditions comprise a variation in pH level, salt level, or both pH level and salt level.

4. The method of claim 3, wherein the mixed mode chromatography resin comprises a methacrylic polymer with tryptophan as a ligand.

5. The method of claim 4, wherein the hydrophobic interaction chromatography resin comprises a methacrylic polymer and a butyl ligand.

6. The method of claim 1, wherein the elution conditions comprise a step variation in pH level, salt level, both pH level and salt level, Hofmeister ion level, both pH and Hofmeister ion level, buffer concentration, buffer composition, both buffer concentration and composition, and combinations thereof.

7. The method of claim 6, wherein the mixed mode chromatography resin comprises a methacrylic polymer with tryptophan as a ligand.

8. The method of claim 6, wherein the hydrophobic interaction chromatography resin comprises a methacrylic polymer and a butyl ligand.

9. The method of claim 1, wherein the mixed mode chromatography resin comprises a methacrylic polymer with tryptophan as a ligand.

10. The method of claim 1, wherein the hydrophobic interaction chromatography resin comprises a methacrylic polymer and a butyl ligand.

11. The method of claim 1, wherein the biological sample is cell supernatant.

12. The method of claim 11, wherein the cell is transfected with a κλ bispecific expression vector comprising one γ1 heavy chain cDNA sequence, one κ light chain cDNA sequence, and one λ cDNA sequence.

13. The method of claim 1, wherein the separation means comprises use of a hydrophobic interaction chromatography resin followed by use of a mixed mode chromatography resin.

14. The method of claim 13, wherein the hydrophobic interaction chromatography resin comprises a methacrylic polymer and a butyl ligand, and wherein the mixed mode chromatography resin comprises a methacrylic polymer with tryptophan as a ligand.

15. The method of claim 1, wherein the separation means comprises use of a mixed mode chromatography resin followed by use of a hydrophobic interaction chromatography resin.

16. The method of claim 15, wherein the mixed mode chromatography resin comprises a methacrylic polymer with tryptophan as a ligand, and wherein the hydrophobic interaction chromatography resin comprises a methacrylic polymer and a butyl ligand.

* * * * *